United States Patent
Meralli et al.

(10) Patent No.: US 10,039,706 B2
(45) Date of Patent: Aug. 7, 2018

(54) COSMETIC COMPOSITION COMPRISING AT LEAST ONE PARTICULAR AMPHOTERIC POLYMER AND AN ANTIDANDRUFF AGENT

(75) Inventors: Sabina Meralli, Fresnes (FR); Bénédicte Fallou, Pollionnay (FR)

(73) Assignee: L'OREAL, Paris (FR)

( * ) Notice: Subject to any disclaimer, the term of this patent is extended or adjusted under 35 U.S.C. 154(b) by 346 days.

(21) Appl. No.: 14/128,481

(22) PCT Filed: Jun. 22, 2012

(86) PCT No.: PCT/EP2012/062096
§ 371 (c)(1),
(2), (4) Date: Feb. 25, 2014

(87) PCT Pub. No.: WO2012/175679
PCT Pub. Date: Dec. 27, 2012

(65) Prior Publication Data
US 2014/0161759 A1   Jun. 12, 2014

Related U.S. Application Data

(60) Provisional application No. 61/528,721, filed on Aug. 29, 2011.

(30) Foreign Application Priority Data

Jun. 23, 2011   (FR) ...................... 11 55554

(51) Int. Cl.
| | | |
|---|---|---|
| *A61K 8/81* | (2006.01) | |
| *A61K 8/49* | (2006.01) | |
| *A61Q 5/00* | (2006.01) | |
| *A61Q 5/02* | (2006.01) | |
| *A61Q 5/12* | (2006.01) | |
| *A61K 8/34* | (2006.01) | |
| *A61K 8/42* | (2006.01) | |
| *A61K 8/58* | (2006.01) | |

(52) U.S. Cl.
CPC .............. *A61K 8/817* (2013.01); *A61K 8/347* (2013.01); *A61K 8/42* (2013.01); *A61K 8/4933* (2013.01); *A61K 8/58* (2013.01); *A61K 8/8158* (2013.01); *A61Q 5/006* (2013.01); *A61Q 5/02* (2013.01); *A61Q 5/12* (2013.01)

(58) Field of Classification Search
CPC .......... A61K 8/817; A61K 8/8158; A61Q 5/12
See application file for complete search history.

(56) References Cited

U.S. PATENT DOCUMENTS

| | | |
|---|---|---|
| 6,375,939 B1 | 4/2002 | Dubief |
| 6,451,300 B1 | 9/2002 | Dunlop |
| 2004/0197287 A1 | 10/2004 | Kaczvinsky, Jr. |
| 2005/0276778 A1 | 12/2005 | Chen |

FOREIGN PATENT DOCUMENTS

| | | | | |
|---|---|---|---|---|
| EP | 1 064 916 A1 | | 1/2001 | |
| EP | 1407757 A1 | * | 4/2004 | ............ A61K 8/496 |
| WO | 2007/031756 A1 | | 3/2007 | |

OTHER PUBLICATIONS

"Conditioning Polymers Provide Multiple Benefits," Personal Care Magazine, Mar. 2011 <http://www.personalcaremagazine.com/Print.aspx?Story=7937> [retrieved Oct. 21, 2011], 3 pages.
International Search Report and Written Opinion dated Jul. 8, 2014, issued in corresponding International Application No. PCT/EP2012/062096, filed Jun. 22, 2012, 9 pages.
"Lubrizol & Nalco Present Naturally Derived Polymers for Skin & Hair Care at in-cosmetics 2011," SpecialChem, Mar. 30, 2011, <http://www.specialchem4cosmetics.com/services/news.aspx?id=6389> [retrieved Mar. 5, 2012, paragraph [0004]-paragraph [0005].

* cited by examiner

*Primary Examiner* — Kyle A Purdy
(74) *Attorney, Agent, or Firm* — Christensen O'Connor Johnson Kindness PLLC

(57) ABSTRACT

The present invention relates to a cosmetic composition comprising: (a) one or more antidandruff agents, and (b) one or more amphoteric polymers comprising a repetition of: (i) one or more units derived from a monomer of (meth) acrylamide type, (ii) one or more units derived from a monomer of (meth)acrylamidoalkyltrialkylammonium type, (iii) one or more units derived from an acidic monomer of (meth)acrylic acid type. The invention also relates to a cosmetic process for treating keratin fibers using such a composition, and to a cosmetic use for facilitating the styling and/or for improving the suppleness, smoothness and/or disentangling of the hair.

17 Claims, No Drawings

COSMETIC COMPOSITION COMPRISING AT LEAST ONE PARTICULAR AMPHOTERIC POLYMER AND AN ANTIDANDRUFF AGENT

The present invention relates to a cosmetic composition for treating keratin fibres, in particular human keratin fibres such as the hair, comprising one or more particular amphoteric polymers and one or more antidandruff agents.

The present invention also relates to a cosmetic process for treating keratin fibres using such a composition and also to a cosmetic use of the said composition.

Numerous haircare compositions containing one or more antidandruff agents have been proposed in the prior art to combat the formation of dandruff.

Now, antidandruff shampoo users often have more or less sensitized hair, i.e. hair that is damaged or embrittled by the action of external atmospheric agents such as light and bad weather, and/or mechanical or chemical treatments such as brushing, combing, dyeing, bleaching, permanent-waving and/or relaxing. These users are thus in search of compositions that have both a good antidandruff effect and good cosmetic properties especially in terms of conditioning of the hair.

In order to improve the cosmetic properties of keratin fibre care compositions, for example those intended to be applied to sensitized hair, it is known practice to introduce into these compositions cosmetic agents known as conditioning agents, which are intended mainly to repair or limit the harmful or undesirable effects induced by the various treatments or attacking factors to which hair fibres are more or less repeatedly subjected. These conditioning agents may, of course, also improve the cosmetic behaviour of natural hair.

Thus, users of antidandruff compositions who have dyed or damaged hair often resort to haircare treatments, and most particularly to treating shampoos combining a silicone and a cationic polymer. These treating shampoos have the advantage of washing the hair, just like a standard shampoo, while at the same time giving the hair conditioning properties, which are particularly sought for the treatment of sensitized hair. Furthermore, these products are frequently used by users and do not require an additional treatment step, which may prove to be burdensome or a constraint in certain cases.

These shampoos combining a silicone and a cationic polymer give a sensation of fluidity and lightness, especially due to the use of the silicones. However, following the repeated use of this type of shampoo, a "build-up" effect may appear, which is manifested by a sensation of lankness of the keratin fibres and a laden, dirty and/or greasy feel and visual appearance. This "build-up" effect is due to the successive deposition of the conditioning agent(s) on the fibres, without the agent previously deposited having been correctly removed. Thus, the deposit of conditioning agent is more and more thick, leading to lankness of the fibres.

Users of antidandruff compositions are thus also seeking to obtain a fluid conditioning effect on keratin fibres, without any lankness effect in the course of the applications, and with a long-lasting sensation of cleanliness of the said fibres. A sensation of regularity of the cosmetic feel obtained, especially homogeneity of the feel from the root to the end of the keratin fibres, is also sought.

There is thus a need to develop cosmetic compositions that have good antidandruff efficacy while at the same time satisfactorily conditioning the hair, and especially giving the hair good properties in terms of the lightness, smoothness, sheen, feel and disentangling of the hair, without making the fibres lank after repeated use of the composition.

Compositions are also sought which are stable over time, which have good working properties (which especially are easy to apply and to remove by rinsing and which, where appropriate, have good lathering properties).

The Applicant has now discovered, surprisingly, that a combination of an antidandruff agent with a particular amphoteric polymer makes it possible to achieve the objectives outlined above.

One subject of the present invention is thus a cosmetic composition comprising:
(a) one or more antidandruff agents, and
(b) one or more amphoteric polymers comprising a repetition of:
(i) one or more units derived from a monomer of (meth) acrylamide type,
(ii) one or more units derived from a monomer of (meth) acrylamidoalkyltrialkylammonium type, and
(iii) one or more units derived from an acidic monomer of (meth)acrylic acid type.

This composition makes it possible especially to obtain homogeneous cosmetic effects on the fibres, without any "build-up" effect or any lankness of the head of hair. The hair, including fibres that are sparingly to very sensitized, are soft, shiny and supple, with a long-lasting sensation of cleanliness, and are easy to style. This composition also makes it possible to obtain a satisfactory volume of the head of hair and, for curly hair, good curl definition.

The present invention also relates to a cosmetic process for treating keratin materials, especially human keratin fibres such as the hair, which consists in applying to the keratin materials a composition according to the invention.

In particular, the composition according to the invention may be rinsed out or left on, and applied with or without the effect of heat.

Preferably, the compositions according to the invention are used as shampoo for washing and conditioning the hair, or as haircare products.

A subject of the present invention is also the use of the composition according to the invention for improving the styling, suppleness, smoothness and/or disentangling of the hair.

It should be noted that the compositions according to the invention are also stable on storage, both at room temperature (20-25° C.) and at 45° C., especially as regards their visual aspect and their viscosity.

For the purposes of the present invention, the term "stable" means that the visual aspect and the viscosity of these compositions do not change substantially over time under storage test conditions, for example at room temperature (20° C.-25° C.) and/or at 45° C. and/or at 4° C. for two months following their manufacture.

Other subjects, characteristics, aspects and advantages of the invention will emerge even more clearly on reading the description and examples that follow.

In the text hereinbelow, unless otherwise indicated, the limits of a range of values are included in that range, especially in the expressions "between" and "ranging from . . . to . . . ".

In the text hereinbelow, the term "at least one" is equivalent to "one or more".

The antidandruff agents that may be used in the composition according to the invention may be any active agent that is useful for preventing the appearance of dandruff, for limiting its amount and/or for eliminating it entirely. Thus, the antidandruff agent may be chosen from antifungal agents and/or antibacterial agents.

The antidandruff agent(s) that may be used according to the invention may be chosen more particularly from:

1) pyridinethione salts, especially the calcium, magnesium, barium, strontium, zinc, cadmium, tin and zirconium salts. The zinc salt of pyridinethione is particularly preferred. The zinc salt of pyridinethione is sold especially under the name Omadine zinc by the company Olin;

2) the trihalocarbamides of formula:

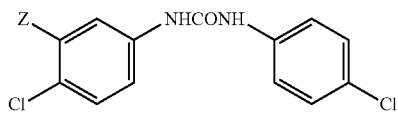

in which Z represents a halogen atom such as chlorine or a $C_1$-$C_4$ trihaloalkyl group such as $CF_3$;

3) triclosan, represented by the formula:

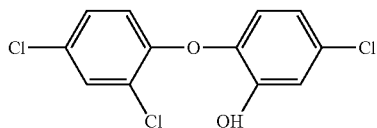 [SMILES: Oc1cc(Cl)ccc1Oc1ccc(Cl)cc1Cl]

4) azole compounds such as climbazole, ketoconazole, clotrimazole, econazole, isoconazole and miconazole;

5) antifungal polymers such as amphotericin B or nystatin;

6) selenium sulfides, in particular those of formula $S_xSe_{8-x}$, x ranging from 1 to 7, and preferably selenium disulfide;

7) 2-pyridone derivatives especially such as piroctone olamine;

8) ellagic acid (or 2,3,7,8-tetrahydroxy(1)benzopyrano(5, 4,3-cde)(1)benzopyran-5,10-dione), ethers thereof, ellagic acid salts and salts of its ethers, and preferably ellagic acid or a salt thereof chosen from the alkali metal or alkaline-earth metal salts, especially the sodium, potassium, calcium or magnesium salts;

9) other antidandruff agents are sulfur in its various forms, cadmium sulfide, allantoin, coal or wood tars and derivatives thereof, in particular cade oil, salicylic acid, undecylenic acid, fumaric acid, and allylamines such as terbinafine.

Preferentially examples of antidandruff agents that may especially be mentioned include zinc pyrithione, salicylic acid, selenium disulfide and ellagic acid, and mixtures thereof.

The composition according to the invention advantageously comprises from 0.001% to 10% by weight, preferably from 0.1% to 5% by weight and even more preferentially from 0.2% to 2% by weight of antidandruff agent(s) relative to the total weight of the composition.

The composition according to the present invention contains one or more amphoteric polymers comprising a repetition of:

(i) one or more units derived from a monomer of (meth) acrylamide type, (ii) one or more units derived from a monomer of (meth) acrylamidoalkyltrialkylammonium type, (iii) one or more units derived from an acidic monomer of (meth)acrylic acid type.

Preferably, the units derived from a monomer of (meth) acrylamide type (i) of the amphoteric polymer are units of structure (I) below:

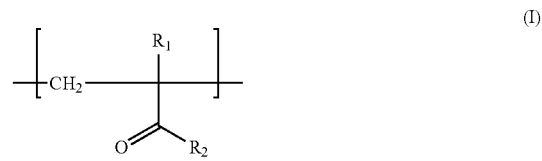

in which:

$R_1$ denotes H or $CH_3$, $R_2$ is chosen from an amino, dimethylamino, tert-butylamino or dodecylamino radical, or —NH—$CH_2$OH.

Preferably, the amphoteric polymer of the invention comprises a repetition of only one unit of formula (I).

The unit derived from a monomer of (meth)acrylamide type of formula (I) in which $R_1$ denotes H and $R_2$ is an amino radical is particularly preferred. It corresponds to the acrylamide monomer per se.

Preferably also, the units derived from a monomer of (meth)acrylamidoalkyltrialkylammonium type (ii) of the amphoteric polymer are units of structure (II) below:

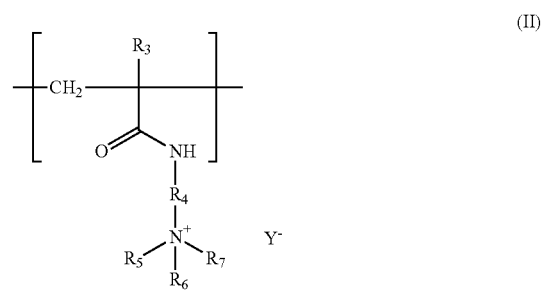

in which:

$R_3$ denotes H or $CH_3$, $R_4$ denotes a group $(CH_2)_k$ with k being an integer ranging from 1 to 6 and preferably from 2 to 4;

$R_5$ and $R_6$, and $R_7$, which may be identical or different, each denote an alkyl group containing from 1 to 4 carbon atoms;

$Y^-$ is an anion such as bromide, chloride, acetate, borate, citrate, tartrate, bisulfate, bisulfite, sulfate or phosphate.

Among these units derived from a monomer of (meth) acrylamidoalkyltrialkylammonium the ones that are preferred are those derived from the methacrylamidopropyltrimethylammonium chloride monomer, for which $R_3$ denotes a methyl radical, k is equal to 3, $R_5$, $R_6$ and $R_7$ denote a methyl radical, and $Y^-$ denotes a chloride anion.

Preferably, the amphoteric polymer of the invention comprises a repetition of only one unit of formula (II).

Finally, the units derived from an acidic monomer of (meth)acrylic acid type (iii) of the amphoteric polymer are preferentially chosen from the units of formula (III):

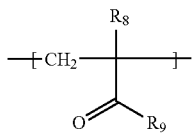
(III)

in which:
R₈ denotes H or CH₃,
R₉ denotes a hydroxyl radical or a radical —NH—C(CH₃)₂—CH₂—SO₃H.

The preferred units of formula (III) correspond to the acrylic acid, methacrylic acid and 2-acrylamino-2-methyl-propanesulfonic acid monomers.

Preferably, the unit derived from an acidic monomer of (meth)acrylic acid type is that derived from acrylic acid, for which R₈ denotes a hydrogen atom and R₉ denotes a hydroxyl radical.

The acidic monomer(s) of (meth)acrylic acid type may be non-neutralized or partially or totally neutralized with an organic or mineral base.

Preferably, the amphoteric polymer of the invention comprises a repetition of only one unit of formula (III).

According to one preferred embodiment of the invention, the amphoteric polymer(s) comprise at least 30 mol % of units derived from a monomer of (meth)acrylamide type. Preferably, they comprise from 30 mol % to 70 mol % and more preferably from 40 mol % to 60 mol % of units derived from a monomer of (meth)acrylamide type.

The contents of units derived from a monomer of (meth)acrylamidoalkyltrialkylammonium type may advantageously be the following: from 10 mol % to 60 mol % and preferentially from 20 mol % to 55 mol %.

The contents of units derived from an acidic monomer of (meth)acrylic acid type may advantageously be the following: from 1 mol % to 20 mol % and preferentially from 5 mol % to 15 mol %.

According to one particularly preferred embodiment of the invention, the amphoteric polymer comprises:
from 30 mol % to 70 mol % and more preferably from 40 mol % to 60 mol % of units derived from a monomer of (meth)acrylamide type,
from 10 mol % to 60 mol % and preferentially from 20 mol % to 55 mol % of units derived from a monomer of (meth)acrylamidoalkyltrialkylammonium type, and
from 1 mol % to 20 mol % and preferentially from 5 mol % to 15 mol % of units derived from an acidic monomer of (meth)acrylic acid type.

The amphoteric polymer(s) according to the present invention may also comprise additional units, other than the units derived from a monomer of (meth)acrylamide type, of (meth)acrylamidoalkyltrialkylammonium type and of (meth)acrylic acid type as described above.

According to one preferred embodiment of the invention, the amphoteric polymer(s) consist solely of units derived from monomers (i) of (meth)acrylamide type, (ii) of (meth)acrylamidoalkyltrialkylammonium type and (iii) of (meth)acrylic acid type.

As examples of amphoteric polymers that are particularly preferred, mention may be made of acrylamide/methacrylamidopropyltrimethylammonium chloride/acrylic acid terpolymers. Such polymers are listed in the CTFA dictionary. International Cosmetic Ingredient Dictionary, 10th edition 2004, under the name Polyquaternium 53. Corresponding products are especially sold under the names Merquat 2003 or Merquat 2003 PR by the company Nalco.

The amphoteric polymer according to the invention may conventionally be prepared by polymerization starting with its various monomers, according to techniques known to those skilled in the art and especially by radical polymerization.

The amphoteric polymer(s) are generally present in the composition according to the invention in an amount of between 0.01% and 10% by weight, preferably between 0.02% and 5% by weight, and more particularly between 0.05% and 1% by weight, relative to the total weight of the composition.

According to one preferred embodiment, the composition according to the present invention also comprises one or more surfactants chosen from anionic surfactants, amphoteric or zwitterionic surfactants, nonionic surfactants and cationic surfactants.

The term "anionic surfactant" means a surfactant comprising, as ionic or ionizable groups, only anionic groups. These anionic groups are preferably chosen from $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2^-$, $PO_2^{2-}$, $POH$ and $PO^-$ groups.

As examples of anionic surfactants that may be used in the composition according to the invention, mention may be made of alkyl sulfates, alkyl ether sulfates, alkylamido ether sulfates, alkylarylpolyether sulfates, monoglyceride sulfates, alkylsulfonates, alkylamidesulfonates, alkylarylsulfonates, α-olefin sulfonates, paraffin sulfonates, alkylsulfosuccinates, alkylether sulfosuccinates, alkylamide sulfosuccinates, alkylsulfoacetates, acylsarcosinates, acylglutamates, alkylsulfosuccinamates, acylisethionates and N—($C_1$-$C_4$)alkyl N-acyltaurates, salts of alkyl monoesters of polyglycoside-polycarboxylic acids, acyllactylates, D-galactoside uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds (unless otherwise mentioned) comprising from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids can be selected from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, the ammonium salts, the amine salts and in particular the amino alcohol salts or the alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts, and in particular sodium or magnesium salts, are preferably used.

The anionic surfactants that may be present may be mild anionic surfactants, i.e. anionic surfactants without a sulfate function.

As regards the mild anionic surfactants, mention may be made in particular of the following compounds and salts thereof, and also mixtures thereof:

polyoxyalkylenated alkyl ether carboxylic acids;
polyoxyalkylenated alkylaryl ether carboxylic acids;
polyoxyalkylenated alkylamido ether carboxylic acids, in particular those comprising 2 to 50 ethylene oxide groups;
alkyl-D-galactoside uronic acids;
acylsarcosinates, acylglutamates; and
alkylpolyglycoside carboxylic esters.

Mention may be made most particularly of polyoxyalkylenated carboxylic acid alkyl ethers, for instance carboxylic acid lauryl ether (4.5 OE) sold, for example, under the name Akypo RLM 45 CA from Kao.

The anionic surfactant(s) may be present in a proportion of from 1% to 50% by weight, preferably from 2% to 25% by weight, particularly from 5% to 25% by weight and even more particularly from 8% to 20% by weight relative to the total weight of the composition.

The amphoteric or zwitterionic surfactant(s) that may be used in the present invention may especially be optionally quaternized secondary or tertiary aliphatic amine derivatives, in which the aliphatic group is a linear or branched chain containing from 8 to 22 carbon atoms, the said amine derivatives containing at least one anionic group, for instance a carboxylate, sulfonate, sulfate, phosphate or phosphonate group.

Mention may be made in particular of ($C_8$-$C_{20}$)alkylbetaines, sulfobetaines, ($C_8$-$C_{20}$ alkyl)amido($C_3$-$C_8$ alkyl) betaines and ($C_8$-$C_{20}$ alkyl)amido($C_6$-$C_8$ alkyl)sulfobetaines.

Among the optionally quaternized secondary or tertiary aliphatic amine derivatives that can be used, as defined above, mention may also be made of the compounds of respective structures (A1) and (A2) below:

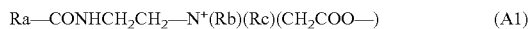

$$Ra-CONHCH_2CH_2-N^+(Rb)(Rc)(CH_2COO-) \quad (A1)$$

in which:
Ra represents a $C_{10}$-$C_{30}$ alkyl or alkenyl group derived from an acid Ra—COOH preferably present in hydrolysed coconut oil, a heptyl, nonyl group or undecyl group,
Rb represents a β-hydroxyethyl group, and
Rc represents a carboxymethyl group;
and

$$Ra'-CONHCH_2CH_2-N(B)(B') \quad (A2)$$

in which:
B represents —$CH_2CH_2OX'$,
B' represents —$(CH_2)_z$-Y', with z=1 or 2,
X' represents the group —$CH_2$—COOH, $CH_2$—COOZ', —$CH_2CH_2$—COOH, —$CH_2CH_2$—COOZ', or a hydrogen atom,
Y' represents —COOH, —COOZ', the group —$CH_2$—CHOH—$SO_3H$ or —$CH_2$—CHOH—$SO_3Z'$,
Z' represents an ion derived from an alkali metal or alkaline-earth metal, such as sodium, an ammonium ion or an ion derived from an organic amine.
Ra' represents a $C_{10}$-$C_{30}$ alkyl or alkenyl group of an acid Ra'—COOH which is preferably present in coconut oil or in hydrolysed linseed oil, or an alkyl group, especially a $C_{17}$ group, and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid and cocoamphodipropionic acid.

By way of example, mention may be made of the cocoamphodiacetate sold by the company Rhodia under the trade name Miranol® C2M Concentrate.

Among the amphoteric or zwitterionic surfactants mentioned above, use is preferably made of ($C_8$-$C_{20}$ alkyl) betaines such as cocoylbetaine, and ($C_8$-$C_{20}$ alkyl)amido ($C_3$-$C_8$ alkyl)betaines such as cocamidopropylbetaine, and mixtures thereof. More preferentially, the amphoteric or zwitterionic surfactant(s) are chosen from cocoylamidopropylbetaine and cocoylbetaine.

When they are present, the amount of the amphoteric or zwitterionic surfactant(s) preferably ranges from 0.05% to 30% by weight, more preferentially from 0.5% to 20% by weight and better still from 1% to 10% by weight relative to the total weight of the composition.

Examples of nonionic surfactants that may be used in the compositions of the present invention are described, for example, in the *Handbook of Surfactants* by M. R. Porter, published by Blackie & Son (Glasgow and London), 1991, pp. 116-178. They are especially chosen from fatty alcohols, fatty α-diols, fatty ($C_{1-20}$)alkylphenols and fatty acids, these compounds being polyethoxylated, polypropoxylated or polyglycerolated and containing at least one fatty chain comprising, for example, from 8 to 18 carbon atoms, the number of ethylene oxide or propylene oxide groups possibly ranging especially from 2 to 50, and the number of glycerol groups possibly ranging especially from 2 to 30.

Mention may also be made of condensates of ethylene oxide and of propylene oxide with fatty alcohols; polyethoxylated fatty amides preferably having from 2 to 30 ethylene oxide units, polyglycerolated fatty amides containing on average 1 to 5, and in particular 1.5 to 4 glycerol groups, ethoxylated fatty acid esters of sorbitan containing from 2 to 30 ethylene oxide units, fatty acid esters of sucrose, fatty acid esters of polyethylene glycol, ($C_{6-24}$ alkyl)polyglycosides, N—($C_{6-24}$ alkyl)glucamine derivatives, amine oxides such as ($C_{10-14}$ alkyl)amine oxides or N—($C_{10-14}$ acyl)aminopropylmorpholine oxides.

When they are present, the amount of the nonionic surfactant(s) preferably ranges from 0.01% to 20% by weight and better still from 0.1% to 10% by weight relative to the total weight of the composition.

The cationic surfactant(s) that may be used in the composition according to the present invention comprise in particular salts of optionally polyoxyalkylenated primary, secondary or tertiary fatty amines, quaternary ammonium salts, and mixtures thereof.

Examples of quaternary ammonium salts that may especially be mentioned include:
those corresponding to the general formula (VII) below:

in which the groups $R_8$ to $R_{11}$, which may be identical or different, represent a linear or branched aliphatic group comprising from 1 to 30 carbon atoms or an aromatic group such as aryl or alkylaryl, at least one of the groups $R_8$ to $R_{11}$ comprising from 8 to 30 carbon atoms and preferably from 12 to 24 carbon atoms. The aliphatic groups may comprise heteroatoms such as, in particular, oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkylacetate, $C_1$-$C_{30}$ hydroxyalkyl, $X^-$ is an anionic counterion chosen from halides, phosphates, acetates, lactates, ($C_1$-$C_4$)alkyl sulfates, and ($C_1$-$C_4$)alkyl- or ($C_1$-$C_4$)alkylarylsulfonates.

Preference is given, among the quaternary ammonium salts of formula (VII), on the one hand, to tetraalkylammonium chlorides, for instance dialkyldimethylammonium or alkyltrimethylammonium chlorides in which the alkyl group comprises approximately from 12 to 22 carbon atoms, in particular behenyltrimethylammonium chloride, distearyldimethylammonium chloride, cetyltrimethylammonium chloride or benzyldimethylstearylammonium chloride, or also, on the other hand, to distearoylethylhydroxyethylmethylammonium methosulfate, dipalmitoylethylhydroxyethylammonium methosulfate or distearoylethylhydroxyethylammonium methosulfate, or also, finally, to palmitylamidopropyltrimethylammonium chloride or stearamidopropyldimethyl(myristyl acetate)ammonium chloride, sold under the name Ceraphyl® 70 by Van Dyk.

quaternary ammonium salts of imidazoline, for instance those of formula (VIII) below:

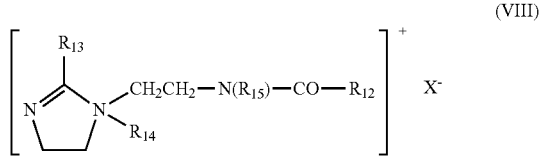

(VIII)

in which:

$R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom, a $C_1$-$C_4$ alkyl group, $X^-$ is an anion chosen from the group of halides, phosphates, acetates, lactates, ($C_1$-$C_4$)alkyl sulfates and ($C_1$-$C_4$)alkyl- or ($C_1$-$C_4$)alkylarylsulfonates.

$R_{12}$ and $R_{13}$ preferably denote a mixture of alkenyl or alkyl groups comprising from 12 to 21 carbon atoms, for example tallow fatty acid derivatives, $R_{14}$ denotes a methyl group, and $R_{15}$ denotes a hydrogen atom. Such a product is, for example, sold under the name Rewoquat® W 75 by the company Rewo;

quaternary diammonium or triammonium salts, in particular of formula (IX) below:

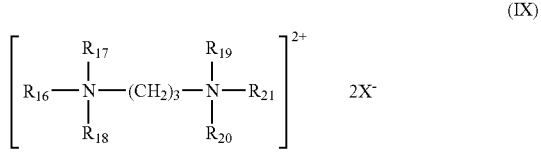

(IX)

in which $R_{16}$ denotes an alkyl group comprising approximately from 16 to 30 carbon atoms, which is optionally hydroxylated and/or interrupted with one or more oxygen atoms;

$R_{17}$ is chosen from hydrogen, an alkyl group comprising from 1 to 4 carbon atoms or a group —$(CH_2)_3$—$N^+(R_{16a})(R_{17a})(R_{18a})$;

$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and $X^-$ is an anionic counterion chosen from the group of halides, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts comprising one or more ester functions, for instance those of formula (X) below:

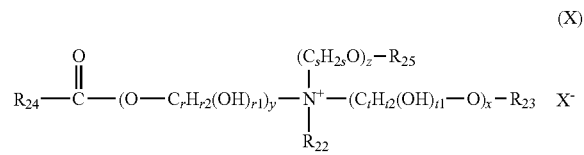

(X)

in which:

$R_{22}$ is chosen from $C_1$-$C_6$ alkyl and $C_1$-$C_6$ hydroxyalkyl or dihydroxyalkyl groups, $R_{23}$ is chosen from:

the group

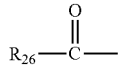

linear or branched, saturated or unsaturated $C_1$-$C_{22}$ hydrocarbon-based groups $R_{27}$, a hydrogen atom, $R_{25}$ is chosen from:

the group

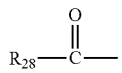

linear or branched, saturated or unsaturated $C_1$-$C_6$ hydrocarbon-based groups $R_{29}$, a hydrogen atom, $R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6, r1 and t1, which may be identical or different, are equal to 0 or 1, r2+r1=2r and t1+t2=2t, y is an integer ranging from 1 to 10, x and z, which may be identical or different, are integers ranging from 0 to 10, $X'^-$ is a simple or complex, organic or mineral anion, with the proviso that the sum x+y+z is from 1 to 15, that when x is 0, then $R_{23}$ denotes $R_{27}$ and that when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z ranges from 1 to 10.

When $R_{23}$ is a hydrocarbon-based group $R_{27}$, it may be long and may contain from 12 to 22 carbon atoms, or may be short and may contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

x and z, which may be identical or different, are preferably 0 or 1.

y is advantageously equal to 1.

Preferably, r, s and t, which may be identical or different, equal 2 or 3, and even more particularly are equal to 2.

The anion $X'^-$ is preferably a halide, preferably chloride, bromide or iodide, a ($C_1$-$C_4$)alkyl sulfate or a ($C_1$-$C_4$)alkyl- or ($C_1$-$C_4$)alkylaryl-sulfonate. However, it is possible to use methanesulfonate, phosphate, nitrate, tosylate, an anion derived from an organic acid, such as acetate or lactate, or any other anion that is compatible with the ammonium containing an ester function.

The anion $X'^-$ is even more particularly chloride, methyl sulfate or ethyl sulfate.

Use is made more particularly, in the composition according to the invention, of the ammonium salts of formula (X) in which:
$R_{22}$ denotes a methyl or ethyl group,
x and y are equal to 1,
z is equal to 0 or 1,
r, s and t are equal to 2,
$R_{23}$ is chosen from:
the group

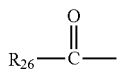

methyl, ethyl or $C_{14}$-$C_{22}$ hydrocarbon-based groups;
a hydrogen atom,
$R_{25}$ is chosen from:
the group

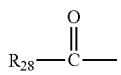

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and more particularly from linear or branched, saturated or unsaturated $C_{13}$-$C_{17}$ alkyl and alkenyl groups.

The hydrocarbon-based groups are advantageously linear.

Among the compounds of formula (X), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

It is also possible to use the ammonium salts containing at least one ester function that are described in U.S. Pat. Nos. 4,874,554 and 4,137,180.

Use may also be made of behenoylhydroxypropyltrimethylammonium chloride sold by the company KAO under the name Quartamin BTC 131.

Preferably, the ammonium salts containing at least one ester function contain two ester functions.

Among the cationic surfactants present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

When the composition contains one or more cationic surfactants, their content preferably ranges from 0.05% to 10% by weight, more preferentially from 0.1% to 5% by weight and better still from 0.5% to 5% by weight relative to the total weight of the composition.

According to a particularly preferred embodiment, the composition according to the invention comprises one or more anionic surfactants and one or more amphoteric or zwitterionic surfactants.

Preferably, the total amount of surfactants in the composition according to the invention ranges from 3% to 50% by weight, more preferentially from 5% to 30% by weight and better still from 8% to 20% by weight relative to the total weight of the composition.

Preferably, the composition according to the invention is aqueous and comprises at least 30% by weight and preferably at least 50% by weight of water relative to the total weight of the composition.

The composition according to the invention may also contain one or more organic solvents that are liquid at room temperature (25° C.) and at atmospheric pressure (760 mmHg, i.e. $1.013 \times 10^5$ Pa). Preferably, the liquid organic solvent(s) are chosen from $C_1$-$C_4$ lower alcohols, such as ethanol, isopropanol, tert-butanol or n-butanol, polyols such as propylene glycol, hexylene glycol and glycerol, and polyol ethers, and mixtures thereof.

When the composition of the invention is aqueous or contains an aqueous phase, its pH is generally between 2 and 9 and in particular between 3 and 8. Preferably, the pH is less than 7. Even more preferentially, it ranges from 3 to 6.

It may be adjusted to the desired value by means of acidifying or basifying agents usually used in cosmetics for this type of application, or alternatively using standard buffer systems.

Among the acidifying agents, use may be made of mineral or organic acids such as hydrochloric acid, orthophosphoric acid, sulfuric acid, carboxylic acids, for instance acetic acid, tartaric acid, citric acid, lactic acid or malic acid, amino acids and sulfonic acids.

Among the basifying agents, examples that may be mentioned include aqueous ammonia, alkali metal carbonates, alkanolamines, such as mono-, di- and triethanolamines and derivatives thereof, amino acids, sodium hydroxide, potassium hydroxide and the compounds of the following formula:

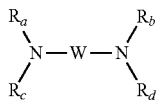

in which W is a propylene residue optionally substituted with a hydroxyl group or a $C_1$-$C_4$ alkyl group; $R_a$, $R_b$, $R_c$ and $R_d$, which may be identical or different, represent a hydrogen atom or a $C_1$-$C_4$ alkyl or $C_1$-$C_4$ hydroxyalkyl group.

Preferably, the pH modifiers may be chosen from alkaline agents, such as aqueous ammonia, monoethanolamine, diethanolamine, triethanolamine, 1,3-propanediamine, 2-amino-2-methyl-1-propanol or an alkaline hydroxide, or else acidifying agents, such as phosphoric acid, hydrochloric acid or citric acid.

The composition according to the present invention may also contain one or more silicones, and especially one or more non-volatile liquid silicones such as a non-volatile linear polydimethylsiloxane (PDMS).

In the context of the invention, the term "non-volatile linear polydimethylsiloxane (PDMS)" means a polydimethylsiloxane with a viscosity of greater than or equal to 5 cSt at 25° C., especially a silicone oil, with a vapour pressure of less than 0.1 mmHg at 25° C. According to one particular embodiment, this viscosity is between 5 cSt and 1 000 000 cSt, preferably between 5 cSt and 100 000 cSt and even more preferentially from 100 to 10 000 cSt.

The composition according to the present invention may also contain one or more other volatile or non-volatile silicones, which may or may not be organomodified with organic groups such as quaternized or non-quaternized amino groups or thiol groups.

The silicone(s) may be present in the composition according to the invention in an amount ranging from 0.01% to 10% by weight and preferably from 0.02% to 5% by weight relative to the total weight of the composition.

The composition according to the present invention may also contain one or more thickeners, which may be chosen especially from cellulose-based thickeners, for example hydroxyethylcellulose, hydroxypropylcellulose and carboxymethylcellulose, guar gum and derivatives thereof, for example the hydroxypropyl guar sold by the company Rhodia under the reference Jaguar HP 105, gums of microbial origin, such as xanthan gum and scleroglucan gum, synthetic thickeners such as crosslinked acrylic acid or acrylamidopropanesulfonic acid homopolymers, for example Carbomer, nonionic, anionic, cationic or amphoteric associative polymers, for instance the polymers sold under the names Pemulen TR1 or TR2 by the company Goodrich, Salcare SC90 by the company Ciba, Aculyn 22, 28, 33, 44 or 46 by the company Rohm & Haas, and Elfacos T210 and T212 by the company Akzo.

The compositions according to the invention may also contain one or more additives chosen from ceramides, vitamins and provitamins including panthenol, water-soluble and liposoluble, silicone or non-silicone sunscreens, nacreous agents and opacifiers, sequestrants, $C_{12}$-$C_{30}$ fatty alcohols, oily or waxy fatty esters such as isopropyl myristate, myristyl myristate, cetyl palmitate and stearyl stearate; mineral, plant or synthetic oils such as α-olefins or avocado oil, rapeseed oil, apricot oil, camellina oil or liquid petroleum jelly; solubilizers, antioxidants, anti-seborrhoeic agents, hair-loss counteractants and/or hair restorers, penetrants, fragrances, peptizers and preserving agents, or any other additive conventionally used in the cosmetics field.

These additives may be present in the composition according to the invention in an amount ranging from 0 to 20% by weight relative to the total weight of the composition.

A person skilled in the art will take care to select these optional additives and amounts thereof so that they do not harm the properties of the compositions of the present invention.

The cosmetic compositions of the invention may be transparent or translucent, i.e. these compositions allow a transmittance at 600 nm of greater than 85%, better still greater than 90% and even better still greater than 94%.

They may also be nacreous with compounds such as, for example, ethylene glycol or polyethylene glycol mono- or distearates, distearyl ether or β-cyclodextrin.

The compositions according to the invention may, in a non-limiting manner, be in the form of shampoos, care products to be applied, where appropriate, before and/or after shampooing or dyeing or permanent-waving, or hair dyeing, bleaching, permanent-waving, relaxing or styling products.

According to a first preferred embodiment, the composition according to the invention is in the form of a shampoo.

In this case, it advantageously contains:
one or more antidandruff agents as described above,
one or more amphoteric polymers as described above,
one or more anionic surfactants in a content ranging from 5% to 25% by weight and preferably from 8% to 20% by weight relative to the total weight of the composition,
optionally, one or more amphoteric or zwitterionic surfactants, in a content ranging from 0.5% to 20% by weight and better still from 1% to 10% by weight relative to the total weight of the composition, and
optionally, one or more nonionic surfactants, in a content ranging from 0.01% to 20% by weight relative to the total weight of the composition.

In a second preferred embodiment, the composition according to the invention is in the form of a haircare product.

In this case, it advantageously contains:
one or more antidandruff agents as described above,
one or more amphoteric polymers as described above, and
one or more cationic surfactants in a content ranging from 0.05% to 10% by weight relative to the total weight of the composition.

The present invention also relates to a cosmetic process for treating keratin fibres, such as the hair, which consists in applying to the hair an effective amount of a composition as described above.

This application may or may not be followed by a rinsing operation.

When the application of the composition is followed by rinsing, the leave-on time of the composition on the keratin materials ranges from a few seconds to 60 minutes, better still from 5 seconds to 30 minutes, even better still from 10 seconds to 10 minutes.

Whether in rinse-out mode or leave-in mode, the application of the composition may take place in the presence or absence of heat. The heating device may be a hairdryer, a hood dryer, a curling iron or a flat iron. The heating temperature may be between 40° C. and 220° C.

Preferably, the compositions according to the invention are used as antidandruff shampoos for washing and conditioning the hair.

The compositions according to the invention are also used for facilitating the styling and/or for improving the suppleness, smoothness and/or disentangling of the hair.

The examples that follow serve to illustrate the invention without, however, being limiting in nature.

EXAMPLES

In the following examples, all the amounts are given as mass percentages of active material relative to the total weight of the composition.

The shampoo compositions A and B according to the invention were prepared from the compounds indicated in the table below.

| Compositions | A | B |
|---|---|---|
| Sodium lauryl sulfate | 4 | 4 |
| Sodium lauryl ether sulfate (2.2 OE) | 11 | 10.9 |
| Polyquaternium-53 [(1)] | 0.77 | 0.2 |
| Zinc pyrithione [(2)] | 1 | 1 |
| Carboxyvinyl polymer [(3)] | 0.3 | 0.3 |
| Coconut acid monoethanolamide | 1.8 | 2 |
| Ethylene glycol distearate | 1.5 | 1 |
| Polydimethylsiloxane containing trimethylsilyl end groups [(4)] | 0.75 | — |
| Glycerol | 2 | 2 |
| Sodium benzoate | 0.5 | 0.5 |
| Sodium chloride | 1.23 | 1.18 |
| Salicylic acid | 0.2 | 0.2 |
| Fragrance | qs | qs |
| pH agent | qs pH = 5.3 | qs pH = 5.3 |
| Water | qs 100% | qs 100% |

[(1)] sold under the trade name Merquat 2003PR by the company Nalco
[(2)] sold under the trade name Zinc omadine pyrithione 48% DSP COSM NE by the company Arch Chemical
[(3)] sold under the trade name Carbopol 980 Polymer by the company Lubrizol
[(4)] sold under the trade name Wacker Belsil DM 60 000 by the company Wacker Compositions A and B are clear and stable over time, both at room temperature and at 45° C.

These compositions are used as a shampoo, by applying to wet hair, and then, after working into a lather and leaving to stand on the hair for a few minutes, the composition is removed from the head of hair by rinsing with water.

Compositions A and B have a very good antidandruff effect and lead to good cosmetic properties, especially to good conditioning properties in terms of smoothness and disentangling, while at the same time maintaining good lightness of the hair, without a lank effect. The hair is also easier to style.

The invention claimed is:

1. Cosmetic composition comprising:
    (a) one or more antidandruff agents, and
    (b) one or more amphoteric polymers comprising a repetition of:
        (i) one or more units derived from a monomer of acrylamide or methacrylamide having a structure (I) below:

in which:
    $R_1$ denotes H or $CH_3$,
    $R_2$ is $NH_2$,
(ii) one or more units derived from a monomer of (meth)acrylamidoalkyltrialkylammonium type having a structure (II) below:

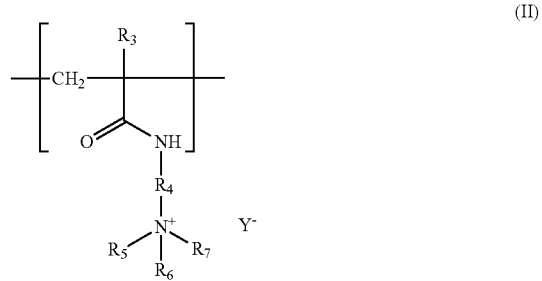

in which:
    $R_3$ denotes H or $CH_3$,
    $R_4$ denotes a group $(CH_2)_k$ with k being an integer ranging from 1 to 6;
    $R_5$, $R_6$, and $R_7$, which may be identical or different, each denotes an alkyl group containing from 1 to 4 carbon atoms;
    $Y^-$ is an anion, and
(iii) one or more units derived from an acidic monomer of (meth)acrylic acid type having a structure (III) below:

in which:
    $R_8$ denotes H or $CH_3$, and
    $R_9$ denotes a hydroxyl radical or a radical —NH—$C(CH_3)_2$—$CH_2$—$SO_3H$.

2. Composition according to claim 1, characterized in that the antidandruff agent(s) are selected from:
1) pyridinethione salts;
2) the trihalocarbamides of formula:

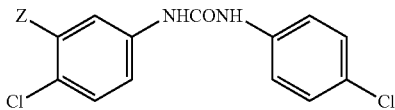

in which Z represents a halogen atom or a $C_1$-$C_4$ trihaloalkyl group;
3) triclosan, represented by the formula:

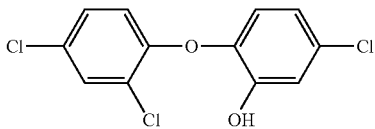 [SMILES: Oc1cc(Cl)ccc1Oc1ccc(Cl)cc1Cl]

4) azole compounds;
5) antifungal polymers;
6) selenium sulfides of formula $S_xSe_{8-x}$, x ranging from 1 to 7;
7) 2-pyridone derivatives;
8) ellagic acid, ethers thereof, ellagic acid salts and salts of its ethers; and
9) sulfur in its various forms, cadmium sulfide, allantoin, coal or wood tars and derivatives thereof.

3. Composition according to claim 1, characterized in that the composition comprises from 0.001% to 10% by weight of antidandruff agent(s), relative to the total weight of the composition.

4. Composition according to claim 1, comprising one or more units derived from acrylamide.

5. Composition according to claim 1, characterized in that the units derived from a monomer of (meth)acrylamidoalkyltrialkylammonium type (ii) of the amphoteric polymer are derived from methylacrylamidopropyltrimethylammonium chloride.

6. Composition according to claim 1, characterized in that the units derived from an acidic monomer of (meth)acrylic acid type (iii) of the amphoteric polymer are derived from acrylic acid.

7. Composition according to claim 1, characterized in that the amphoteric polymer comprises:
from 30 mol % to 70 mol % of units derived from a monomer of acrylamide or methacrylamide,
from 10 mol % to 60 mol % of units derived from a monomer of (meth)acrylamidoalkyltrialkylammonium type, and
from 1 mol % to 20 mol % of units derived from an acidic monomer of (meth)acrylic acid type.

8. Cosmetic composition according to claim 1, characterized in that the amphoteric polymer(s) are present in a content ranging from 0.01% to 10% by weight, relative to the total weight of the composition.

9. Composition according to claim 1, characterized in that the composition also comprises one or more surfactants selected from anionic surfactants, amphoteric surfactants, zwitterionic surfactants, nonionic surfactants, and cationic surfactants.

10. Composition according to claim 9, characterized in that the composition comprises one or more anionic surfactants selected from alkyl sulfates, alkyl ether sulfates, alkylamido ether sulfates, alkylaryl polyether sulfates, monoglyceride sulfates, alkyl sulfonates, alkylamide sulfonates, alkylaryl sulfonates, alpha-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N—($C_1$-$C_4$)alkyl N-acyltaurates, salts of alkyl monoesters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids, corresponding non-salified forms of these compounds; and alkyl and acyl groups of these compounds comprising from 6 to 24 carbon atoms; wherein the aryl group denotes a phenyl group.

11. Composition according to claim 9, characterized in that the composition comprises one or more anionic surfactants in a content ranging from 1% to 50% by weight, relative to the total weight of the composition.

12. Composition according to claim 9, characterized in that the composition comprises one or more amphoteric or zwitterionic surfactants in an amount ranging from 0.05% to 30% by weight, relative to the total weight of the composition.

13. Cosmetic process for treating keratin materials, characterized in that the process consists in applying to the keratin materials a composition according to claim 1 and then in optionally rinsing the composition out after an optional leave-on time, in the presence or absence of heat.

14. Cosmetic process for cleansing and conditioning keratin fibres, characterized in that the process consists in applying to the keratin fibres an antidandruff shampoo composition as defined in claim 1.

15. Cosmetic process for facilitating the styling and/or for improving the suppleness, smoothness and/or disentangling of hair, characterized in that the process consists in applying to the hair a composition as defined in claim 1.

16. Composition according to claim 1, characterized in that the antidandruff agent(s) are selected from zinc pyrithione, salicylic acid, selenium disulfide, ellagic acid, and mixtures thereof.

17. Composition according to claim 12, characterized in that the one or more amphoteric or zwitterionic surfactants are selected from ($C_8$-$C_{20}$)alkylbetaines, ($C_8$-$C_{20}$)alkylamido($C_3$-$C_8$)alkylbetaines, and mixtures thereof.

* * * * *